United States Patent
Kogure et al.

(10) Patent No.: US 6,650,987 B2
(45) Date of Patent: Nov. 18, 2003

(54) ROAD FRICTION COEFFICIENTS ESTIMATING APPARATUS FOR VEHICLE

(75) Inventors: Masaru Kogure, Tokyo (JP); Yutaka Hiwatashi, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/987,408

(22) Filed: Nov. 14, 2001

(65) Prior Publication Data

US 2002/0087251 A1 Jul. 4, 2002

(30) Foreign Application Priority Data

Nov. 16, 2000 (JP) ........................................ 2000/350092

(51) Int. Cl.$^7$ .............................................. G06F 17/00
(52) U.S. Cl. .......................................... 701/80; 73/105
(58) Field of Search ............................... 701/70, 72, 73, 701/74, 80, 104, 105

(56) References Cited

U.S. PATENT DOCUMENTS

| | | | | |
|---|---|---|---|---|
| 5,229,955 | A | * 7/1993 | Nishiwaki et al. | 701/40 |
| 6,163,747 | A | * 12/2000 | Matsuno | 701/80 |
| 6,349,256 | B1 | * 2/2002 | Kin et al. | 701/72 |
| 6,473,682 | B1 | * 10/2002 | Nakamura | 701/74 |
| 2001/0029419 | A1 | * 10/2001 | Matsumoto et al. | 701/80 |
| 2002/0002437 | A1 | * 1/2002 | Matsuno | 701/80 |
| 2002/0072841 | A1 | * 6/2002 | Kogure | 701/80 |
| 2002/0072842 | A1 | * 6/2002 | Kogure | 701/80 |

FOREIGN PATENT DOCUMENTS

| | | |
|---|---|---|
| EP | 1 072 490 A2 | 1/2001 |
| JP | 08-002274 | 1/1996 |
| JP | 2001-39289 | 2/2001 |
| JP | 2001-043352 | 2/2001 |

* cited by examiner

*Primary Examiner*—Gary Chin
(74) *Attorney, Agent, or Firm*—McGinn & Gibb, PLLC

(57) ABSTRACT

A road friction coefficient estimating apparatus primarily includes an adaptive control road friction coefficient estimating section and an actual value comparison road friction coefficient estimating section. The adaptive control road friction coefficient estimating section inputs signals indicative of a road surface condition with low friction coefficient from a wiper switch, low outside air temperature judging section and the like and estimates an accurate road friction coefficient even under the low friction coefficient road surface condition. When the vehicle travels at high speeds, the actual value comparison road friction coefficient estimating section renders a road friction coefficient estimating value by a yaw rate comparison method gradually close to a road friction coefficient of an asphalted road surface. When a signal IMAGE HALT indicative of a road surface totally covered with snow is inputted, the actual value comparison road friction coefficient estimating section renders the road friction coefficient estimating value gradually close to a low side road friction coefficient produced by the adaptive control road friction coefficient estimating section. Further, when the vehicle travels at high speeds and the signal IMAGE HALT is inputted, the road friction coefficient estimating value is rendered moderately, gradually close to the low side road friction coefficient.

17 Claims, 6 Drawing Sheets

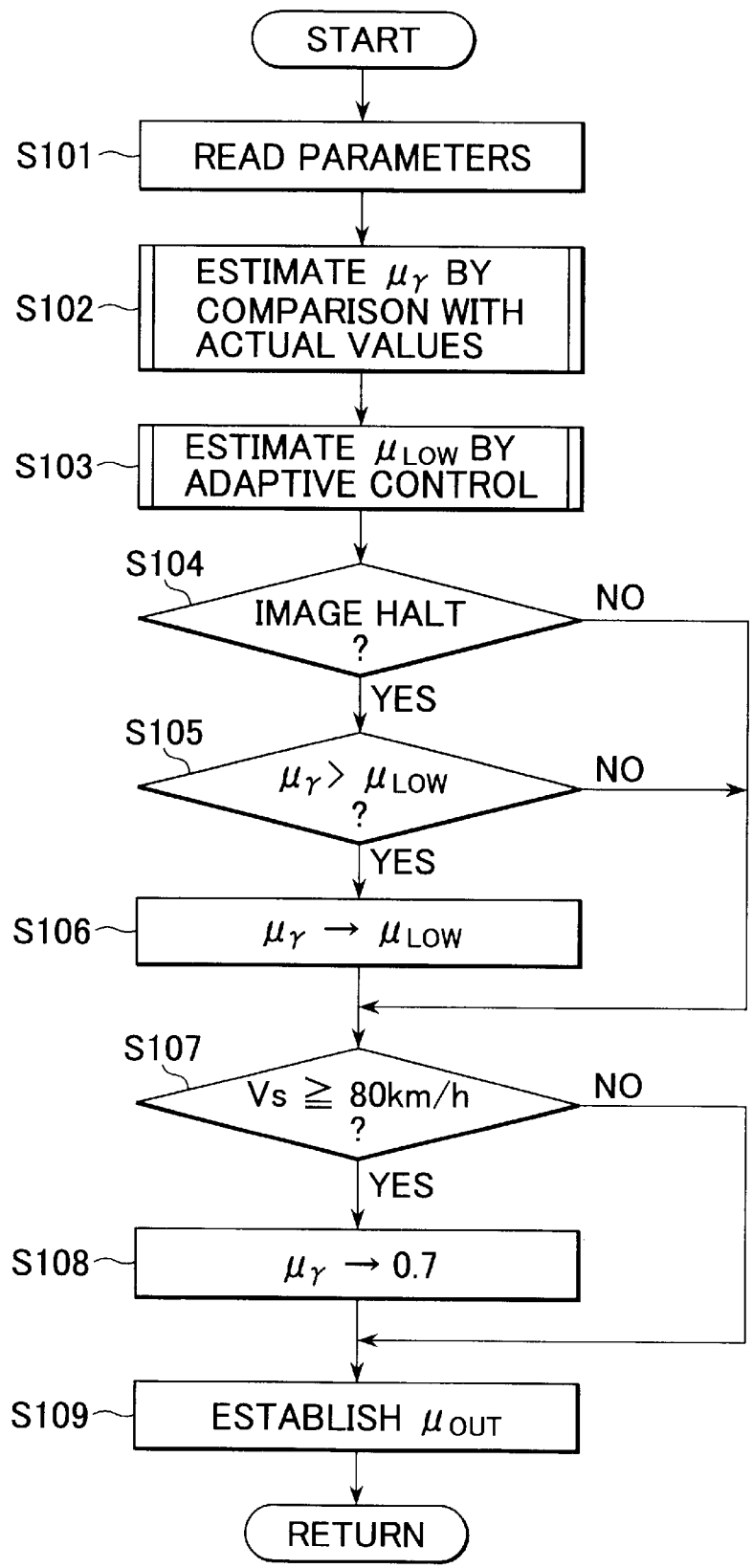

US 6,650,987 B2

ROAD FRICTION COEFFICIENTS ESTIMATING APPARATUS FOR VEHICLE

BACKGROUND OF THE INVENTION

1. Field of the Invention

The present invention relates to a road friction coefficients estimating apparatus for a vehicle for estimating friction coefficients on road surfaces and more particularly to a road friction coefficients estimating apparatus capable of properly estimating friction coefficients on road surfaces according to traveling conditions.

2. Discussion of Prior Arts

In recent years, numerous vehicle control technologies such as traction control technologies, braking force control technologies, torque distribution control technologies and the like, have been proposed and some of these control technologies have been realized in actual automobile markets. Many of these control technologies use friction coefficients on road surfaces (hereinafter, referred to as "road friction coefficient") for calculation or correction of control parameters. Accordingly, in order to execute the control properly, it is necessary to estimate accurate road friction coefficients.

Several technologies in which road friction coefficients are estimated based on vehicle motion parameters such as lateral acceleration, yaw rate have been proposed. For example, the applicant of the present invention proposes a technology in which road friction coefficients are estimated based on the comparison of an actual yaw rate estimated from an observer with a high friction coefficient road reference yaw rate calculated using a vehicle motion model on a high friction coefficient road surface and with a low friction coefficient road reference yaw rate calculated using a vehicle motion model on a low friction coefficient road surface respectively in Japanese Patent Application No. Toku-Gan-Hei 11-217508.

However, a road friction coefficient estimating apparatus in which a road friction coefficient is estimated based on conditions of vehicle motion has a problem that especially when the vehicle travels at high speeds, because the change of yaw rate, lateral acceleration and steering angles is very small even under the large effect of road friction coefficients, it is extremely difficult to accurately estimate road friction coefficients by detecting this small change.

SUMMARY OF THE INVENTION

It is an object of the present invention to provide a road friction coefficients estimating apparatus capable of properly establishing road friction coefficients of a vehicle traveling at high speeds.

To achieve the object, the road friction coefficient estimating apparatus for a vehicle comprises a motion parameter detecting means for detecting motion parameters of the vehicle, a traveling circumstance recognition means for detecting traveling circumstances and for outputting a recognition signal indicative of a road surface covered with snow, a low friction coefficient road traveling condition detecting means for detecting a traveling condition indicative of a traveling on a road surface having low friction coefficient, a low side road friction coefficient estimating means for estimating a low side road friction coefficient according to an adaptive control theory and to a vehicle motion model based on the motion parameters and the traveling condition indicative of a traveling on a road surface having low friction coefficient and a road friction coefficient estimating means for estimating a road friction coefficient based on the motion parameters by comparing an actual yaw rate with a high friction coefficient road reference yaw rate and a low friction coefficient road reference yaw rate.

Further, the road friction coefficient estimating means renders the road friction coefficient first estimated by the road friction coefficient estimating means itself gradually close to a road friction coefficient established beforehand of an asphalted road surface when the vehicle travels at high speeds. Further, the road friction coefficient estimating means renders the road friction coefficient first estimated by the road friction coefficient estimating means itself gradually close to the low side road friction coefficient when the recognition signal is inputted. Further, the road friction coefficient estimating means renders the road friction coefficient first estimated by the road friction coefficient estimating means itself gradually close to the low side road friction coefficient when the vehicle travels at high speeds and when the recognition signal is inputted.

BRIEF DESCRIPTION OF THE DRAWINGS

FIG. 6 is a flowchart showing steps for calculating a road friction coefficient estimating value according to an embodiment of the present invention.

DETAILED DESCRIPTION OF PREFERRED EMBODIMENTS

Figure 1:
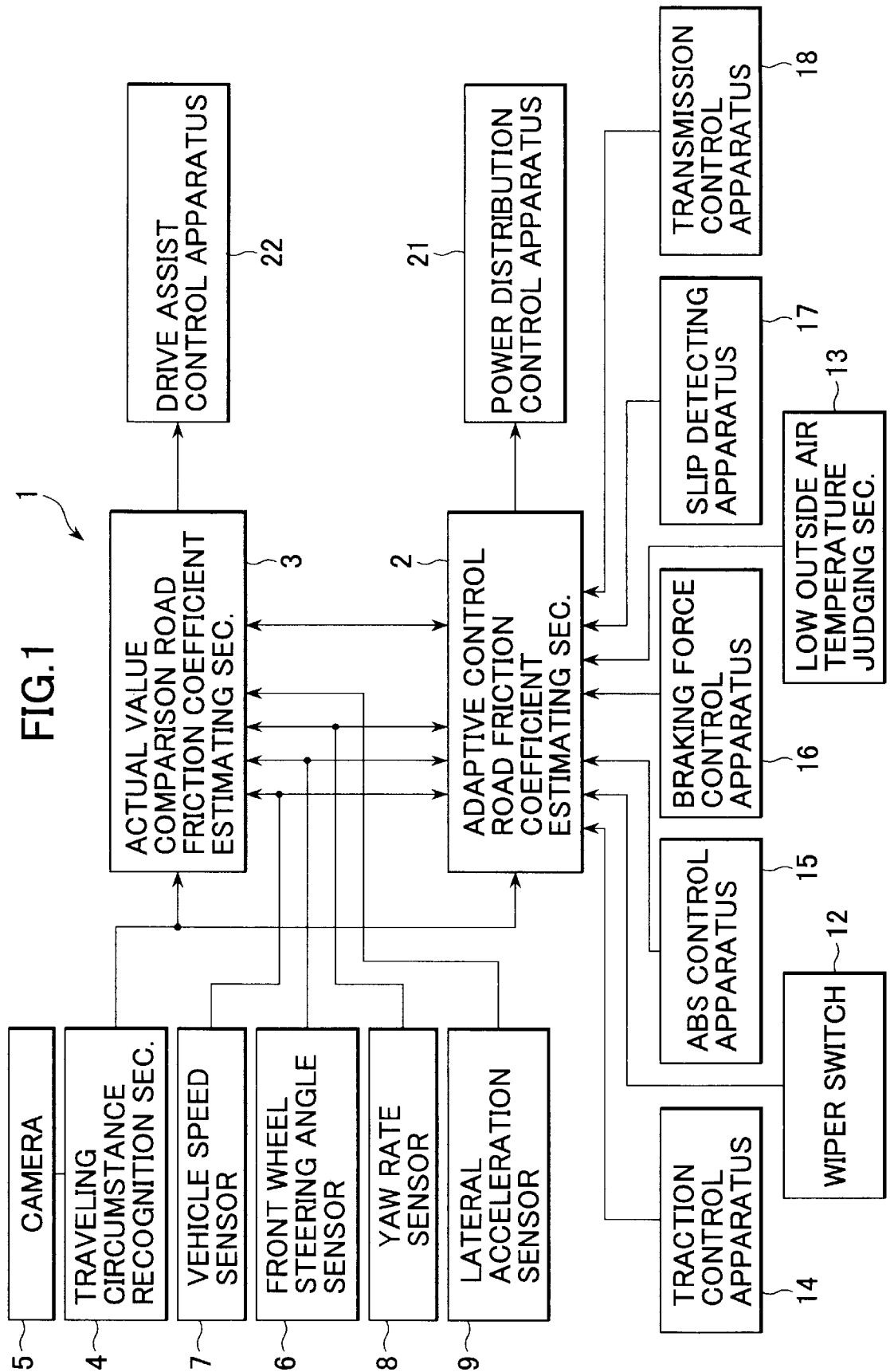
FIG. 1 is a functional block diagram showing a construction of a road friction coefficients estimating apparatus according to an embodiment of the present invention.

Referring now to FIG. 1, reference numeral 1 denotes a road friction coefficients estimating apparatus mounted on a vehicle for estimating road friction coefficients and the road friction coefficients estimating apparatus 1 is constituted by two road friction coefficient estimating sections, an adaptive control road friction coefficient estimating section 2 and an actual value comparison road friction coefficient estimating section 3. These two road friction coefficient estimating sections 2, 3 input a signal indicative of the result of recognition by a traveling circumstance recognition section 4.

The traveling circumstance recognition section 4 serves as a traveling circumstance recognition means in the present invention. A pair of cameras 5 disposed laterally under the ceiling of the passenger compartment take stereoscopic images of outside objects from different view points and distance information is obtained allover the image based on the stereoscopic images by the principle of triangulation. Next, based on the distance information, distance images presenting three dimensional distance distribution are formed. Then, road conditions in front of the vehicle and solid objects (preceding vehicles) are recognized by processing these distance images based on various stored data.

Further, as the applicant of the present invention describes in detail in Japanese Patent Application No. Toku-Gan-Hei 11-216191, when the traveling circumstance recognition section 4 detects a road condition that can be deemed as an overall road surface covered with snow in an observation area established in a specified area on the image obtained from the pair of cameras, the traveling circumstance recognition section 4 has a fail-safe function of outputting a signal "IMAGE HALT". Specifically, the number of brightness edges in the horizontal direction in the observation area and the overall size of brightness are calculated. In case where the number of brightness edges is smaller than a threshold value and the overall size of brightness is greater than a specified value, it is judged that the traveling circumstance is deemed as a totally snow-covered condition and the signal indicating this condition (signal of IMAGE HALT) is outputted to two road friction coefficient estimating sections 2, 3.

The adaptive control road friction coefficient estimating section 2 is also connected with a front wheel steering angle sensor 6, a vehicle speed sensor 7 and a yaw rate sensor 8 and respective sensor values indicative of front wheel steering angle $\delta_{fs}$, vehicle speed $V_s$ and yaw rate $(d\phi/dt)_s$ (yaw angular velocity). A parameter with subscript "S" indicates a value detected by a sensor.

Further, the adaptive control road friction coefficient estimating section 2 is connected with a wiper switch 12, a low outside air temperature judging section 13, a traction control apparatus 14, an antilock brake (ABS) control apparatus 15, a braking force control apparatus 16, a slip detecting apparatus 17 and a transmission control apparatus 18 and inputs working signals from these apparatuses. These apparatuses, wiper switch 12, low outside air temperature judging section 13, traction control apparatus 14, antilock brake (ABS) control apparatus 15, braking force control apparatus 16, slip detecting apparatus 17 and transmission control apparatus 18 output working signals to the adaptive control road friction coefficient estimating section 2 when the vehicle travels on a road surface with low friction coefficient, constituting a low friction coefficient road traveling condition detecting means.

Making brief descriptions about operations of these apparatuses, the wiper switch 12 outputs a working signal to the adaptive control road friction coefficient estimating section 2, when a wiper operates.

The low outside air temperature judging section 13 judges whether or not outside air temperature is low (for example, below 0 degree) and in case of affirmative, a working signal is outputted to the adaptive control road friction coefficient estimating section 2.

The traction control apparatus 14 detects slip rate of respective wheels based on four wheel speeds and when a representative slip rate exceeds a specified value and outputs a specified control signal to a brake drive system and an engine control system to brake or reduce engine torque. The working signal of the traction control apparatus 14 is outputted also to the adaptive control road friction coefficient estimating section 2.

The ABS control apparatus 15 calculates wheel speed, acceleration, deceleration and tentative calculated vehicle speed (when brake pedal is depressed and deceleration of wheel speed is above a specified value, it is judged that the vehicle is in abrupt braking. tentative calculated vehicle speed is a vehicle speed calculated at a specified deceleration with an initial velocity established when the judgment is made) and the like, selects a brake control signal from three hydraulic modes, increasing pressure, holding pressure and decreasing pressure and outputs a selected brake control signal to a brake drive system. Further, the working signal of the ABS control apparatus 15 is outputted to the adaptive control road friction coefficient estimating section 2, too.

The braking force control apparatus 16 calculates differential of target yaw rate based on four wheel speeds, front wheel steering angle, yaw rate and vehicle specifications, and differential of estimated yaw rate when traveling on a low friction coefficient road and deviation between both differentials. Further, the braking force control apparatus 16 calculates deviation between actual yaw rate and target yaw rate. Based on these values, target braking force for correcting an under-steer tendency or an over-steer tendency of the vehicle is calculated. Generally, in order to correct the under steer tendency of a vehicle, it is necessary to apply braking force to a rear inside wheel of a turning circle and in order to correct the over steer tendency, it is necessary to apply braking force to a front outside wheel of a turning circle. The braking force control apparatus 16 selects the braking wheel to which braking force is to be applied and outputs a control signal to the brake drive system to apply the target braking force to the selected braking wheel. This control signal is also outputted to the adaptive control road friction coefficient estimating section 2.

The slip detecting apparatus 17 judges whether or not the vehicle is in a slip condition according to whether or not a rotational speed ratio of an average speed of front left and right wheels to an average speed of rear left and right wheels exceeds a preestablished threshold value. If the slip detecting apparatus 17 judges that the vehicle is in a slip condition, the apparatus outputs a working signal to the adaptive control road friction coefficient estimating section 2.

The transmission control apparatus 18 sends a working signal to the adaptive control road friction coefficient estimating section 2 when a range 1 is selected to raise a towing ability and maneuverability of the vehicle on a road surface with low friction coefficient.

Further, the adaptive control road friction coefficient estimating section 2 calculates a road friction coefficient (road friction coefficient estimating value $\mu_{LOW}$) and outputs the value to a power distribution control apparatus 21 and on the other hand, when a signal of IMAGE HALT is inputted from the traveling circumstance recognition section 4, the value $\mu_{LOW}$ is read by the actual value comparison road friction coefficient estimating section. The power distribution control apparatus 21 controls the driving force distribution between front and rear wheels by controlling differential limiting torque of a center differential (not shown) according to the estimated road friction coefficient.

The adaptive control road friction coefficient estimating section 2 estimates road friction coefficients by the method using an adaptive control which the applicant of the present invention discloses in Japanese Patent Application Laid-open No. Toku-Kai-Hei 8-2274. That is, based on a lateral motion model of a vehicle using front wheel steering angle $\delta_{fs}$, vehicle speed $V_s$, yaw rate $(d\phi/dt)_s$, cornering powers of front and rear wheels are extended up to a nonlinear zone and estimated therein. A road friction coefficient is estimated according to road surface conditions based on the ratio of the estimated cornering powers of front and rear wheels to the equivalent cornering powers of front and rear wheels on a road surface with high friction coefficient.

In this case, with respect to the estimating method of the road friction coefficient, there is a method of estimating road friction coefficients in real time, comparing a yaw rate response based on the equation of vehicle motion with an actual yaw rate and putting equivalent cornering powers as unknown parameters. Specifically, the first road friction coefficient is calculated according the following adaptive control theory on the basis of the parameter adjustment rule.

Figure 2:
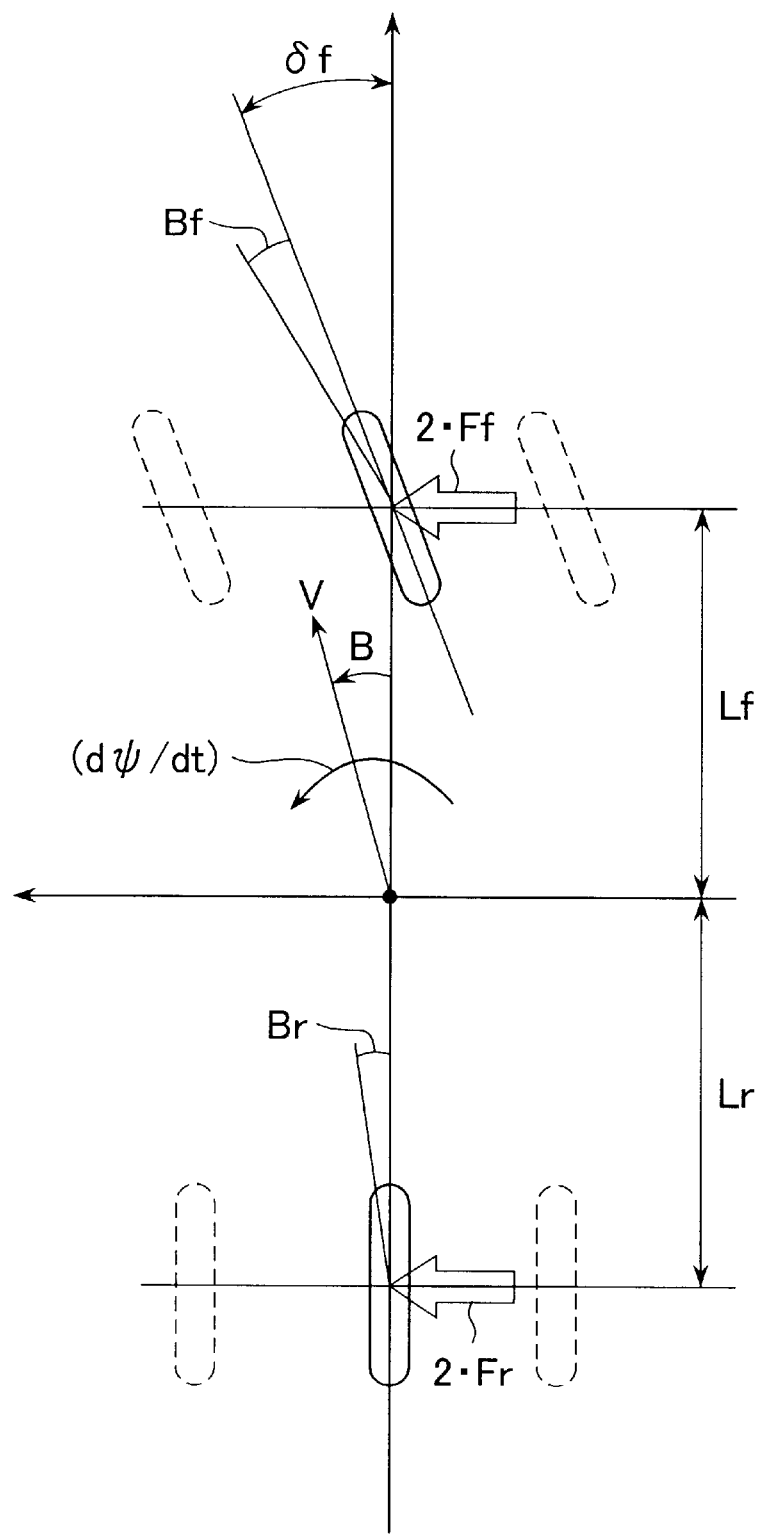
FIG. 2 is a diagram showing a two wheel vehicle model equivalent to a four wheel vehicle.

The equation of lateral transitional motion of a vehicle is expressed using a vehicle motion model illustrated in FIG. 2 as:

$$M \cdot (d^2y/dt^2) = 2 \cdot F_f + 2 \cdot F_r \quad (1)$$

where M is mass of a vehicle; $F_f$, $F_r$ are cornering forces of front and rear wheels, respectively; and $d^2y/dt^2$ is lateral acceleration.

On the other hand, the equation of rotational motion around gravity center of the vehicle is expressed as:

$$I_z \cdot (d^2\phi/dt^2) = 2 \cdot F_f \cdot L_f - 2 \cdot F_r \cdot L_r \quad (2)$$

where $I_z$ is yaw moment of inertia of the vehicle; $L_f$, $L_r$ are distances from the center of gravity to the front and rear wheels, respectively; and $(d^2\phi/dt^2)$ is yaw angular acceleration.

The lateral acceleration $(d^2y/dt^2)$ is expressed as:

$$(d^2y/dt^2) = V \cdot ((d\beta/dt) + (d\phi/dt)) \quad (3)$$

where V is vehicle speed; $\beta$ is slip angle of the vehicle; and $(d\beta/dt)$ is slip angular velocity of the vehicle.

The cornering forces have a response similar to a first-order time lag. In this case, this time lag being neglected and letting the cornering forces be linearized introducing an idea of equivalent cornering power in which suspension characteristic is involved in tire characteristic, the cornering forces are expressed as follows:

$$F_f = -K_f \beta_f \quad (4)$$

$$F_r = -K_r \beta_r \quad (5)$$

where $K_f$, $K_r$ are equivalent cornering powers of front and rear wheels, respectively; and $\beta_f$, $\beta_r$ are lateral slip angles of front and rear wheels, respectively.

Using equivalent cornering powers taking the effect of roll and suspension of the vehicle into consideration, lateral slip angles $\beta_f$, $\beta_r$ are can be simplified as follows:

$$\beta_f = \beta + L_f \cdot (d\phi/dt)/V - \delta_f \quad (6)$$

$$\beta_r = \beta - L_r \cdot (d\phi/dt)/V \quad (7)$$

where $\delta_f$ is steering angle of front wheel.

Various parameters are estimated by expressing the aforesaid equation of motion in state variables and applying the adaptive control theory to the equation according to the parameter adjustment rule. Next, cornering powers of the vehicle are obtained from the parameters thus estimated. There are many parameters for the vehicle such as vehicle mass, yaw inertia moment and the like. In the present invention, these parameters are assumed to be constant. Only cornering powers of tire are assumed to change. There are some reasons why the cornering powers of tire change, a non-linearity of lateral force versus slip angle, an effect of road friction coefficients, an effect of load transference and the like. The cornering powers $K_f$, $K_r$ of front and rear wheels are obtained from the following equations:

$$K_f = (q \cdot I_z \cdot n)/(2 \cdot L_f) \quad (8)$$

$$K_r = (p \cdot I_z + L_f K_f)/L_r \quad (9)$$

where p is a parameter estimated from a change of yaw rate; and q is a parameter estimated from a front wheel steering angle $\delta_f$.

Accordingly, the cornering powers $K_f$, $K_r$ of front and rear wheels are estimated according to the aforesaid equations using front wheel steering angles $\delta_{fs}$, vehicle speed $V_s$ and yaw rate $(d\phi/dt)_s$ by expanding the cornering powers to a non-linear area. Further, a road friction coefficient is calculated by comparing these estimated cornering powers $K_f$, $K_r$ of front and rear wheels with the cornering powers of front and rear wheels on a road surface with high friction coefficient and a road friction coefficient $\mu_{LOW}$ of non-linear area is established accurately based on the above calculated road friction coefficient.

Further, road friction coefficient estimating values $E_f$, $E_r$ of front and rear wheels respectively are expressed as:

$$E_f = K_f / K_{f0} \quad (10)$$

$$E_r = K_r / K_{r0} \quad (11)$$

where $K_{f0}$, $K_{r0}$ are reference equivalent cornering powers (equivalent cornering powers on a road surface with high friction coefficient) of front and rear sides respectively.

Further, letting an average value of the road friction coefficient estimating values $E_f$, $E_r$ of front and rear wheels respectively be a road friction coefficient $\mu_{LOW}$, $$\mu_{LOW} = (E_f + E_r)/2 \quad (12)$$

According to the aforesaid method applying the adaptive control theory of estimating a road friction coefficient, first the control is performed with a present estimated value and as a result how far the estimated value deviates from an actual road friction coefficient is calculated. The amount of the calculated deviation is added to the present estimated value and an accurate value is obtained. That is, the integration is performed based on whether the present estimated value is larger or smaller than the actual one and the estimated value nears the actual one.

Further, when the adaptive control road friction coefficient estimating apparatus 2 inputs a working signal of the wiper switch 12, a judging signal of low outside air temperature of the low outside air judging section 13, a working signal of the traction control apparatus 14, a working signal of the ABS control apparatus 15, a working signal of the braking force control apparatus 16, a slip detecting signal of the slip detecting apparatus 17 and a signal indicative of transmission control apparatus 18's selecting the range 1, in case where the road friction coefficient estimated by the aforesaid adaptive control method exceeds a value established beforehand, the calculation next time starts with an initial value forced to be established to a road friction coefficient on a lower side (for example 0.3).

That is, since the aforesaid road friction coefficient estimating method in the adaptive control road friction coefficient estimating section 2 is basically constituted by the integrating operation, when road friction coefficients fluctuates, in case where an initially estimated road friction coefficient (initial value) greatly differs from an actual road friction coefficient, it takes a long time to obtain a proper road friction coefficient estimating result. Accordingly, in case where at least either of traveling conditions, the vehicle is in a slip condition or the vehicle travels on a road surface with low friction coefficient, is detected, the initial value is established to a road friction coefficient rather on a low side to raise responsibility. Therefore, the adaptive control road friction coefficient estimating section 2 is a low side road friction coefficient estimating means which can accurately estimate a road friction coefficient even on a road surface with a low friction coefficient. Hence, the road friction coefficient estimating value $\mu_{LOW}$ is outputted to the power distribution control apparatus 21 that is expected to fulfill its performance particularly on a low friction coefficient road. Further, when a signal IMAGE HALT inputs from the traveling circumstance recognition section 4, the road friction coefficient estimating value $\mu_{LOW}$ is read by the actual value comparison road friction coefficient estimating section 3.

Further, when a signal indicative of vehicle starting of engine after a long period of parking inputs to the adaptive control road friction coefficient estimating section, an initial road friction coefficient is forcedly established at a value of an intermediate area (for example, $\mu$=0.5) between a high friction coefficient area and a low friction coefficient area and road friction coefficients hereafter are started to be calculated from this intermediate value. A long period in "A long period of parking" means around a period during which a computer of the vehicle is replaced in a repair shop. At a normal starting of engine, the first road friction coefficient is estimated based on the cornering powers previously estimated by a back-up electric source.

On the other hand, the actual value comparison road friction coefficient estimating section 3 serves as a road friction coefficient estimating means in the present invention, to which in addition to the traveling circumstance recognition section 4, front wheel steering angle sensor 6, vehicle speed sensor 7, yaw rate sensor 8 and lateral acceleration sensor 9 are connected.

The actual value comparison road friction coefficient estimating section 3 inputs sensor values of front wheel steering angle $\delta_{fs}$, vehicle speed $V_s$, lateral acceleration $(d^2y/dt^2)_s$, yaw rate $(d\phi/dt)_s$ from respective sensors.

The actual value comparison road friction coefficient estimating section 3 estimates road friction coefficients and outputs the estimated road friction coefficients (road friction coefficient estimating value $\mu_{out}$) to a drive assist control apparatus 22. The drive assist control apparatus 22 performs miscellaneous controls using road friction coefficients (for example, warning control, automatic brake control and the like) associated with cornering of a curve ahead of the vehicle. When the actual value comparison road friction coefficient estimating section 3 inputs a signal of IMAGE HALT from the traveling circumstance recognition section 4, in case where the state continues for a specified time (for example, 90 seconds), the actual value comparison road friction coefficient estimating section 3 reads the road friction coefficient estimating value $\mu_{LOW}$ from the adaptive control road friction coefficient estimating section 2 and renders the estimated road friction coefficient gradually close to the road friction coefficient estimating value $\mu_{LOW}$. Further, in case where the inputted vehicle speed $V_s$ is larger than 80 kilometer/hour and that state continues for more than a specified time, the actual value comparison road friction coefficient estimating section 3 renders the estimated road friction coefficient gradually close to a road friction coefficient value of an ordinary asphalted road surface, for example 0.7. Further, in case where a signal of IMAGE HALT inputs from the traveling circumstance recognition section 4 and the state continues for more than a specified time (for example 90 seconds) and in case where the vehicle speed $V_s$ exceeds 80 kilometer/hour for more than a specified time, the actual value comparison road friction coefficient estimating section 3 reads the road friction coefficient estimating value $\mu_{LOW}$ from the adaptive control road friction coefficient estimating section 2 and renders the estimated road friction coefficient gradually close to the road friction coefficient estimating value $\mu_{LOW}$.

Figure 3:
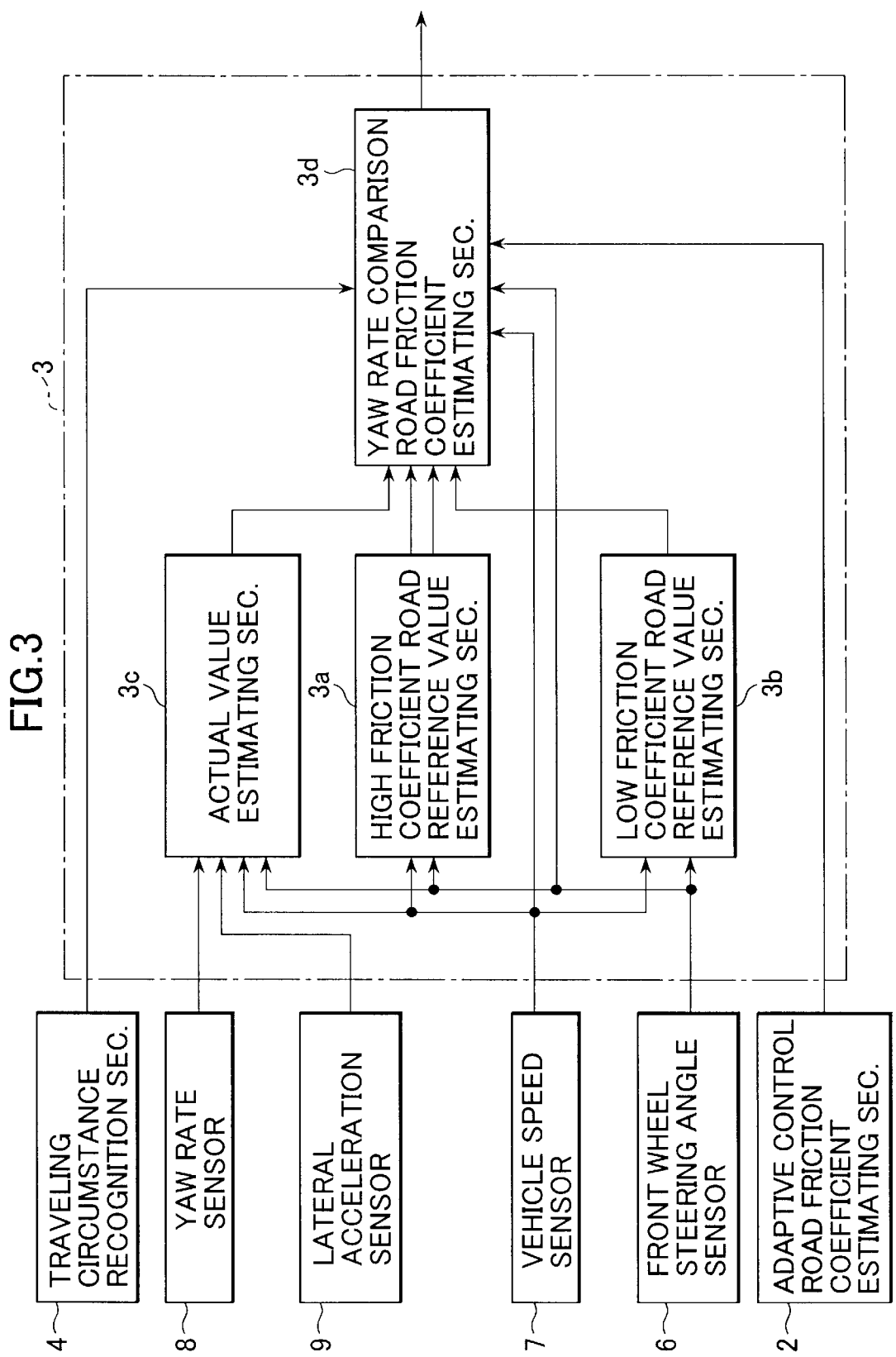
FIG. 3 is a functional block diagram showing a construction of an actual value comparison road friction coefficient estimating section.

As shown in FIG. 3, the actual value comparison road friction coefficient estimating section 3 is constituted by a high friction coefficient road reference value estimating section 3a, a low friction coefficient road reference value estimating section 3b, an actual value estimating section 3c and a yaw rate comparison road friction coefficient estimating section 3d.

The high friction coefficient road reference value estimating section 3a inputs vehicle speed $V_s$ and front wheel steering angle $\delta_{fs}$, calculates high friction coefficient road reference yaw rate $(d\phi/dt)_H$ corresponding to the detected vehicle speed $V_s$ and front wheel steering angle $\delta_{fs}$ according to a vehicle motion model on the basis of an equation of vehicle motion on a road surface with high friction coefficient and outputs the high friction coefficient road reference yaw rate $(d\phi/dt)_H$ to the yaw rate comparison road friction coefficient estimating section 3d.

Further, the high friction coefficient road reference value estimating section 3a outputs high friction coefficient road reference yaw angular acceleration $(d^2\phi/dt^2)_H$, lateral acceleration $(d^2y/dt^2)_H$, in addition to yaw rate $(d\phi/dt)_H$, to the yaw rate comparison road friction coefficient estimating section 3d. Respective parameters with subscription "H" denote parameters on the basis of high friction coefficient reference.

The low friction coefficient road reference value estimating section 3b inputs vehicle speed $V_s$ and front wheel steering angle $\delta_{fs}$, calculates low friction coefficient road reference yaw rate $(d\phi/dt)_L$ corresponding to the detected vehicle speed $V_s$ and front wheel steering angle $\delta_{fs}$ according to a vehicle motion model based on an equation of vehicle motion on a road surface with low friction coefficient and outputs the low friction coefficient road reference yaw rate $(d\phi/dt)_L$ to the yaw rate comparison road friction coefficient estimating section 3d.

Further, the low friction coefficient road reference value estimating section 3b outputs low friction coefficient road reference yaw angular acceleration $(d^2\phi/dt^2)_L$, in addition to yaw rate $(d\phi/dt)_L$, to the yaw rate comparison road friction coefficient estimating section 3d. Respective parameters with subscription "L" denote parameters on the basis of high friction coefficient reference.

The vehicle motion model and the calculation of respective parameters will be described by reference to FIG. 2 The following equation of state is obtained from the aforesaid equations of motion (1) to (7):

$$(dx(t)/dt) = A \cdot x(t) + B \cdot u(t) \tag{13}$$

$$x(t) = [\beta (d\phi/dt)]^T$$

$$u(t) = [\delta_f 0]^T$$

$$A = \begin{bmatrix} a_{11} & a_{12} \\ a_{21} & a_{22} \end{bmatrix}$$

$$B = \begin{bmatrix} b_{11} & b_{12} \\ b_{21} & b_{22} \end{bmatrix}$$

$a_{11} = -2 \cdot (K_f + K_r)/(M \cdot V)$
$a_{12} = -1 - 2 \cdot (L_f \cdot K_f - L_r \cdot K_r)/(M \cdot V^2)$
$a_{21} = -2 \cdot (L_f \cdot K_f - L_r \cdot K_r)/I_z$
$a_{22} = -2 \cdot (L_f^2 \cdot K_f + L_r^2 \cdot K_r)/(I_z \cdot V)$
$b_{11} = 2 \cdot K_f/(M \cdot V)$
$b_{21} = 2 \cdot L_f \cdot K_f/I_z$
$b_{12} = b_{22} = 0$ In the high friction coefficient road reference value estimating section 3a, a high friction coefficient road reference slip angular velocity $(d\phi/dt)_H$ and a high friction coefficient road reference yaw angular acceleration $(d^2\phi/dt^2)_H$ are obtained by calculating $(dx(t)/dt)=[(d\beta/dt)\ (d^2\phi/dt^2)]^T$ in a vehicle operating condition (vehicle speed $V_s$ and front wheel steering angle $\delta_{fs}$) of each moment, when equivalent cornering powers $K_f$, $K_r$ at 1.0 for example of road friction coefficient have been established beforehand in the formula (13). Then, a high friction coefficient road reference vehicle slip angle $\beta_H$ and a high friction coefficient road reference yaw rate $(d\phi/dt)_H$ are obtained by integrating the vehicle slip angular velocity $(d\beta/dt)_H$ and the yaw angular acceleration $(d^2\phi/dt^2)_H$. Further, substituting the high friction coefficient road reference vehicle slip angle $\beta_H$ and high friction coefficient road reference yaw rate $(d\beta/dt)_H$ into the formula (6), a high friction coefficient road reference front wheel slip angle $\beta_{fH}$ is calculated. Further, substituting the vehicle slip angular velocity $(d\beta/dt)_H$ and high friction coefficient road reference yaw rate $(d\phi/dt)_H$ into the formula (3), a high friction coefficient lateral acceleration $(d^2y/dt^2)_H$ is calculated.

Similarly, in the low friction coefficient road reference value estimating section 3b, a low friction coefficient road reference slip angular velocity $(d\beta/dt)_L$ and a low friction coefficient road reference yaw angular acceleration $(d^2\phi/dt^2)_L$ are obtained by calculating $(dx(t)/dt)=[(d\beta/dt)\ (d^2\phi/dt^2)]^T$ in a vehicle operating condition (vehicle speed $V_s$ and front wheel steering angle $\delta_{fs}$) of each moment, when equivalent cornering powers $K_f$, $K_r$ at 0.3 for example of road friction coefficient have been established beforehand in the formula (13). Then, a low friction coefficient road reference vehicle slip angle $\beta_L$ and a low friction coefficient road reference yaw rate $(d\phi/dt)_L$ are obtained by integrating the calculated vehicle slip angular velocity $(d\beta/dt)_L$ and yaw angular acceleration $(d^2\phi/dt^2)_L$. Further, substituting the low friction coefficient road reference vehicle slip angle $\beta_L$ and low friction coefficient road reference yaw rate $(d\phi/dt)_L$ into the formula (6), a low friction coefficient road reference front wheel slip angle $\beta_{fL}$ is calculated.

The actual value estimating section 3c inputs front wheel steering angle $\delta_{fs}$, vehicle speed $V_s$, lateral acceleration $(d^2y/dt^2)_s$ and yaw rate $(d\phi/dt)_s$ and estimates an actual yaw rate $(d\phi/dt)_0$ while the actual behavior of the vehicle is fed back. That is, the actual value estimating section 3c is an observer formed by the vehicle motion model. The actual yaw rate $(d\phi/dt)_0$ estimated in the actual value estimating section 3c is outputted to the yaw rate comparison road friction coefficient estimating section 3d. Further, in addition to the actual yaw rate $(d\phi/dt)_0$, a yaw angular acceleration $(d^2\phi/dt^2)_0$ is outputted to the yaw rate comparison road friction coefficient estimating section 3d. The parameters with subscription "0" denote ones derived from the observer.

Figure 4:
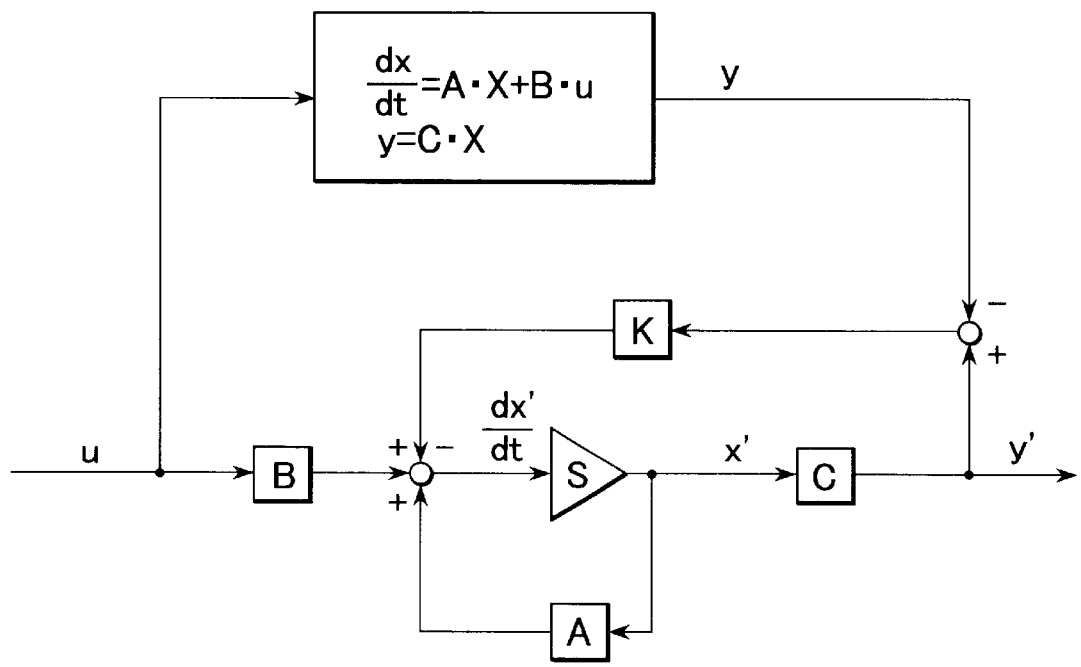
FIG. 4 is a circuit diagram showing a basic construction of an observer.

The constitution of the observer of the embodiment will be described by reference to FIG. 4.

When the output detected by the sensor is expressed as follows:

$$y(t)=C \cdot x(t) \tag{14}$$

The construction of the observer is:

$$(dx'(t)/dt)=(A-K \cdot C) \cdot x'(t)+K \cdot y(t)+B \cdot u(t) \tag{15}$$

x(t) is state variable vector (superscript "'" indicates an estimating value); u(t) is input vector; A, B is coefficient matrix of state equation; y(t) is obsevable sensor output vector and is expressed as:

$$y(t)=[\beta_s (d\phi/dt)_s]^T$$

The vehicle slip angle $\beta_s$ detected by sensor is obtained by integrating the vehicle slip angular velocity $(d\beta/dt)_s$ detected by sensor. The vehicle slip angular velocity $(d\beta/dt)_s$ is obtained from the formula (3) based on the lateral acceleration $(d^2y/dt^2)_s$ detected by sensor and the yaw rate $(d\phi/dt)_s$ detected by sensor; C is matrix (in this embodiment, unit matrix) indicating the relationship between sensor output and state variable and K is feed-back gain matrix that can be arbitrarily established and C, K is expressed respectively as follows:

$$C = \begin{bmatrix} 1 & 0 \\ 0 & 1 \end{bmatrix}$$

$$K = \begin{bmatrix} k_{11} & k_{12} \\ K_{21} & k_{22} \end{bmatrix}$$

Hence, the actual yaw angular acceleration $(d^2\phi/dt^2)_0$ and the actual vehicle slip angular velocity $(d\beta/dt)_0$ are calculated by the observer by the following formulas (16) and (17):

$$(d^2\phi/dt^2)_0 = a_{11} \cdot (d\phi/dt)_0 + a_{12} \cdot \beta_0 + b_{11} \cdot \delta_{fs} + \\ k_{11} \cdot ((d\phi/dt)_s - (d\phi/dt)_0) + \\ k_{12} \cdot (\beta_s - \beta_0) \tag{16}$$

$$(d\beta/dt)_0 = a_{21} \cdot (d\phi/dt)_0 + a_{22} \cdot \beta_0 + \\ k_{21} \cdot ((d\phi/dt)_s - (d\phi/dt)_0) + \\ k_{22} \cdot (\beta_s - \beta_0) \tag{17}$$

Accordingly, an actual yaw rate $(d\phi/dt)_0$ and an actual vehicle slip angle $\beta_0$ are calculated by integrating thus calculated actual yaw angular acceleration $(d^2\phi/dt^2)_0$ and actual vehicle slip angular velocity $(d\beta/dt)_0$, respectively. Further, an actual front wheel slip angle $\beta_{f0}$ is calculated by substituting the actual vehicle slip angle $\beta_0$ and the actual yaw rate $(d\phi/dt)_0$ into the formula (6), respectively.

In the high friction coefficient road reference value estimating section 3a, the low friction coefficient road reference value estimating section 3b and the actual value estimating section 3c, when the vehicle speed Vs=0, the calculation can not be executed due to the division by 0. Hence, when the vehicle travels at extremely low speeds, for example below 10 km/h, the yaw rate and the lateral acceleration are replaced with sensor values respectively. That is, $$(d\phi/dt)_H=(d\phi/dt)_L=(d\phi/dt)_0=(d\phi/dt)_s$$

$$(d^2y/dt^2)_0=(d^2y/dt^2)_s$$

Further, the vehicle slip angle can be expressed from the geometric relationship of the turning on the stationary circle as:

$$\beta_H=\beta_L=\beta_0=\delta_{fs} \cdot L_r/(L_f+L_r)$$

At this time, since no cornering force is generated, the front wheel slip angle becomes 0.

$$\beta_{fH}=\beta_{fL}=\beta_{f0}=0$$

The yaw rate comparison road friction coefficient estimating section 3d inputs front wheel steering angle $\delta_{fs}$, vehicle speed $V_s$, high friction coefficient road reference yaw rate $(d\phi/dt)_H$, high friction coefficient road reference yaw angular acceleration $(d^2\phi/dt^2)_H$, high friction coefficient road reference lateral acceleration $(d^2y/dt^2)_H$, low friction coefficient road reference yaw rate $(d\phi/dt)_L$, low friction coefficient yaw angular acceleration $(d^2\phi/dt^2)_L$, yaw rate $(d\phi/dt)_0$ estimated as an actual value and yaw angular acceleration $(d^2\phi/dt^2)_0$ estimated as an actual value. Further, when an executional condition which will be described hereinafter is satisfied, using high friction coefficient road reference yaw rate $(d\phi/dt)_H$, low friction coefficient road reference yaw rate $(d\phi/dt)_L$, and yaw rate $(d\phi/dt)_0$, a road friction coefficient estimating value obtained this time $\mu_{yn}$ is calculated by comparison of road friction coefficients according to the following formula (18):

$$\mu_{yn}=((\mu_H-\mu_L)\cdot(d\phi/dt)_0+\mu_L\cdot(d\phi/dt)_H-\mu_H\cdot(d\phi/dt)_L)/((d\phi/dt)_H-(d\phi/dt)_L) \quad (18)$$

where $\mu_H$ is a road friction coefficient assumed in the high friction coefficient road reference value estimating section 3a (for example 1.0); and $\mu_L$ is a road friction coefficient assumed in the low friction coefficient road reference value estimating section 3b (for example 0.3).

According to the formula (18), a linear function is formed by high friction coefficient road reference yaw rate $(d\phi/dt)_H$ and low friction coefficient road reference yaw rate $(d\phi/dt)_L$ and a new road friction coefficient $\mu_{yn}$ is obtained by substituting yaw rate $(d\phi/dt)_0$ into this linear function.

Further, a road friction coefficient estimating value $\mu_y$ is obtained by weight-averaging the previously estimated road friction coefficient $\mu_{n-1}$ and the this time estimated road friction coefficient $\mu_{yn}$ for example according to the following formula (19).

$$\mu_y=\mu_{n-1}+\kappa_1\cdot(\mu_{yn}-\mu_{n-1}) \quad (19)$$

where $\kappa_1$ is weight factor and is determined as follows:

$$\kappa_1=0.3\cdot|(d\phi/dt)_H-(d\phi/dt)_L|/|(d\phi/dt)_H| \quad (20)$$

In order to calculate the road friction coefficient estimating value $\mu_y$ in the yaw rate comparison road friction coefficient estimating section 3d, following conditions have been established beforehand.

Condition 1

Since the vehicle motion which inherently belongs to a multiple degrees of freedom system is approximated to the 2-wheel model having a two degrees (lateral transference and motion around vertical axis) of freedom system, the calculation of road friction coefficients is not performed when the vehicle travels at very low speeds or the steering wheel is turned largely, because the difference of vehicle behavior between the model and actual vehicle increases. In this embodiment, the calculation is not executed when the vehicle travels at a speed smaller than 10 km/h or when the absolute value of the steering angle exceeds 500 degrees.

Condition 2

When the absolute value of yaw rate is small, since then the portion of noises, disturbances and the like becomes relatively large, the calculation of road friction coefficients is not performed taking the effects of electric noises of sensor inputs and disturbances not being assumed at modeling into consideration. For example, in case where the absolute value of yaw rate $(d\phi/dt)_0$ is smaller than 1.5 degrees/second, the calculation of road friction coefficients is not performed.

Condition 3

Since the method according to the present invention is the one of estimating road friction coefficients applying the phenomenon that there appears a difference between cornering forces in accordance with road friction coefficients, in case where the cornering forces are small, that is, in case where the absolute value of lateral acceleration is small, the ratio of the effects of noises or disturbances to the effect of road friction coefficients becomes relatively large and therefore in this case the calculation of road friction coefficients is not performed. For example, in case where the absolute value of the high friction coefficient road reference lateral acceleration $(d^2y/dt^2)_H$ is smaller than 0.15 G, the calculation of road friction coefficients is not performed.

Condition 4

The yaw rate response to the steering angle input is delayed depending upon road friction coefficient in some case. When the yaw rate response is delayed, the road friction coefficients estimated have large errors. Accordingly, in case where there is a large delay, the calculation of road friction coefficients is not performed. For example, in case where it is judged that the errors due to delays except at a rise time (a specified period of time from start of generation of yaw rate until convergence of yaw rate) of yaw rate become large, the calculation of road friction coefficients is not performed. A rise of yaw rate is judged from (yaw rate)·(yaw angular acceleration).

Condition 5

In case where the absolute value of the difference between the high friction coefficient road reference yaw rate and low friction coefficient road reference yaw rate is not big enough to eliminate the effect of noises, disturbances and the like, the calculation of road friction coefficients is not performed. For example, in case where the absolute value of the difference between the high friction coefficient road reference yaw rate $(d\phi/dt)_H$ and the low friction coefficient road reference yaw rate $(d\phi/dt)_L$ is smaller than 1 degree/second, the calculation of road friction coefficients is not performed.

Condition 6

To prevent a division by 0 in the formula (20), for example, in case where the absolute value of the high friction coefficient road reference yaw rate $(d\phi/dt)_H$ is smaller than 1 degree/second, the calculation of road friction coefficients is not performed.

Further, the yaw rate comparison road friction coefficient estimating section 3d inputs a signal indicative of traveling circumstance of the vehicle from the traveling circumstance recognition section 4. When a signal of IMAGE HALT is inputted from the traveling circumstance recognition section 4 and in case where the state continues for a specified time (for example 90 seconds), a road friction coefficient estimating value $\mu_{LOW}$ is read from the adaptive control road friction coefficient estimating section 2. If the road friction coefficient estimating value $\mu_y$ estimated in the yaw rate comparison road friction coefficient estimating section 3d is larger than the road friction coefficient estimating value $\mu_{LOW}$ read from the adaptive control road friction coefficient estimating section, the road friction coefficient estimating value $\mu_y$ is rendered gradually close to the road friction coefficient estimating value $\mu_{LOW}$ by passing the road friction coefficient estimating value $\mu_y$ through a first order lag filter having a time constant T1 and this value is outputted as a finally estimated road friction coefficient estimating value $\mu_{out}$. The characteristic of this first order lag filter is exemplified in FIG. 5. The filter has a characteristic, as shown in a portion I of FIG. 5, that the road friction coefficient estimating value $\mu_y$ descends approximately up to a level of the road friction coefficient estimating value $\mu_{LOW}$ outputted from the adaptive control road friction coefficient estimating section 2 for 30 seconds. That is, in case where a signal of IMAGE HALT is inputted from the traveling circumstance recognition section 4, there is high possibility that the vehicle travels on a road surface with low friction coefficient. Because of this, the actual value comparison road friction coefficient estimating section 3 adopts a road friction coefficient estimating value $\mu_{LOW}$ from the adaptive control road friction coefficient estimating section 2 in which an accurate road friction coefficient can be estimated even when the vehicle travels on a road surface with low friction coefficient.

The yaw rate comparison road friction coefficient estimating section 3d, when the inputted vehicle speed $V_s$ shows a high speed traveling, for example, in case where the vehicle speed is larger than 80 kilometer/hour and this state continues for more than specified time, renders the road friction coefficient estimating value $\mu_\gamma$ gradually close to a road friction coefficient of an ordinary asphalted road surface (for example 0.7) by passing the road friction coefficient $\mu_\gamma$ through a first order lag filter having a time constant T2 and outputs this value as a finally estimated road friction coefficient estimating value $\mu_{out}$. This first order lag filter having a time constant T2 has a characteristic of raising the road friction coefficient estimating value $\mu_\gamma$ estimated by the yaw rate comparison road friction coefficient estimating section 3d approximately up to a level of 0.7 in 60 seconds as shown in a portion III of FIG. 5. That is, when the vehicle travels on a high way, even if the road friction coefficient exerts a large effect on the vehicle, there is a very small change in yaw rate, lateral acceleration and steering angle and it is extremely difficult to estimate road friction coefficients accurately by detecting small changes of these parameters. Accordingly, when the vehicle travels at high speeds, the aforesaid characteristic of the first order lag filter prevents to judge the road surface to be a low friction coefficient road.

Figure 5:
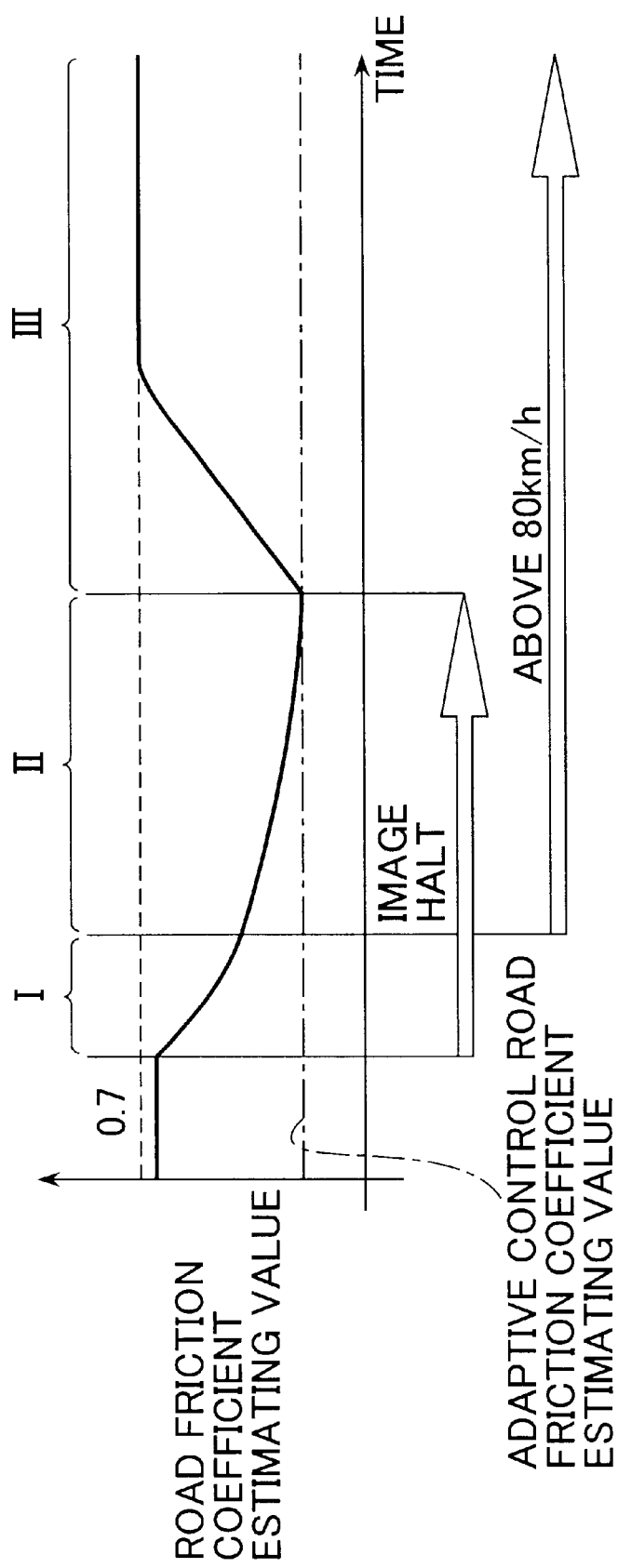
FIG. 5 is a timing chart showing an example of estimation of road friction coefficients.

In case where the yaw rate comparison road friction coefficient estimating section 3d inputs a signal of IMAGE HALT from the traveling circumstance recognition section 4 and the state continues for a specified time (for example 90 seconds) and in case where the inputted vehicle speed Vs indicates a high speed driving, for example, the vehicle travels at more than 80 km/hour, and the state continues for a specified time, the yaw rate comparison road friction coefficient estimating section 3d reads a road friction coefficient estimating value $\mu_{LOW}$ from the adaptive control road friction coefficient estimating section 2. Then, in case where the road friction coefficient estimating value $\mu_\gamma$ estimated in the yaw rate comparison road friction coefficient estimating section 3d is larger than the road friction coefficient estimating value $\mu_{LOW}$, the yaw rate comparison road friction coefficient estimating section 3d passes the road friction coefficient estimating value $\mu_\gamma$ through the first order lag filter with time constant T1 and further passes through the first order lag filter with time constant T2. Since the descending variation of road fiction coefficient estimating value by the first order lag filter with time constant T1 is greater, as shown in FIG. 5, than the rising variation of road fiction coefficient estimating value by the first order lag filter with time constant T2, as shown in a portion II of FIG. 5, the road friction coefficient estimating value $\mu_\gamma$ estimated in the yaw rate comparison road friction coefficient estimating section 3d is rendered moderately, gradually close to the road friction coefficient estimating value $\mu_{LOW}$ estimated in the adaptive control road friction coefficient estimating section 2. Then, this value is outputted as a finally estimated road friction coefficient estimating value $\mu_{out}$. That is, in case where there is high possibility that the road on which the vehicle travels is obviously a low fiction coefficient road, the road friction coefficient estimating value is rendered gradually close to the road friction coefficient estimating value $\mu_{LOW}$, even when the vehicle travels at high speeds.

Next, the estimation of road friction coefficients in the road friction coefficients estimating apparatus 1 will be described using a flowchart of FIG. 6. This program is executed at a specified time interval (for example 10 milliseconds).

First, at a step (hereinafter abbreviated as "S") 101, the parameters are read. In S102, the road friction coefficient estimating value $\mu_\gamma$ is estimated by comparison with actual values, and in S103, the road friction coefficient estimating value $\mu_{LOW}$ is estimated by adaptive control.

At step S104, it is judged whether or not a signal of IMAGE HALT indicating the state of road surface totally covered with snow is continuously inputted for a specified time. In case where the signal of IMAGE HALT is continuously inputted for a specified time, the program goes to S105 wherein the road friction coefficient estimating value $\mu_\gamma$ obtained from the comparison with yaw rate is compared with the road friction coefficient estimating value $\mu_{LOW}$ outputted from the adaptive control road friction coefficient estimating section 2.

If the road friction coefficient estimating value $\mu_\gamma$ obtained by the comparison with yaw rate is larger than the road friction coefficient estimating value $\mu_{LOW}$ from the adaptive control road friction coefficient estimating section 2, the program goes to S106 where the road friction coefficient estimating value $\mu_\gamma$ obtained by the comparison with yaw rate is rendered gradually close to the road friction coefficient estimating value $\mu_{LOW}$ from the adaptive control road friction coefficient estimating section 2.

On the other hand, in case where it is judged that the signal of IMAGE HALT is not inputted, or in case where it is judged that the road friction coefficient estimating value $\mu_\gamma$ by the comparison with yaw rate is smaller than the road friction coefficient estimating value $\mu_{LOW}$ from the adaptive control road friction coefficient estimating section 2, the program skips to S107.

When the program goes from S104, S105 or S106 to S107, it is judged whether or not the vehicle speed $V_s$ is larger than 80 kilometer/hour and the state continues for a specified time. In case where it is judged that the vehicle speed $V_s$ is larger than 80 kilometer/hour, the program goes to S108 where the road friction coefficient estimating value $\mu_\gamma$ obtained by the comparison with yaw rate is rendered gradually close to 0.7 of a road friction coefficient of an ordinary asphalted road surface by passing the road friction coefficient estimating value $\mu_\gamma$ through the first order lag filter having time constant T2.

In case where the program goes to S108 without processing S106, it is judged that the vehicle travels at high speeds and there is no other condition, the road friction coefficient estimating value $\mu_\gamma$ is passed only through the first order lag filter with time constant T2 and rendered gradually close to 0.7.

In case where S106 is processed and further S108 is processed, the road friction coefficient estimating value $\mu_\gamma$ obtained from the comparison with yaw rate is passed through both first order lag filter of time constant T1 and first order lag filter of time constant T2 and rendered moderately, gradually close to the road friction coefficient estimating value $\mu_{LOW}$ outputted from the adaptive control road friction coefficient estimating section 2 by the difference of time constants T1, T2.

When the program goes from S108 to S109, the road friction coefficient estimating value $\mu_\gamma$ based on yaw rate comparison is passed only through the filter of time constant T2 or through both filters of time constants T1, T2 and is established as an output value $\mu_{out}$, the program leaving the routine.

Thus, according to the embodiment of the present invention, the actual value comparison road friction coefficient estimating section 3, when the vehicle travels at high speeds, renders the road friction coefficient estimating value $\mu_\gamma$ obtained from the comparison with yaw rates gradually close to a road friction coefficient estimating value (0.7) established beforehand of asphalted road surface. Further, in case where the vehicle travels at high speeds and the signal of IMAGE HALT is inputted, the road friction coefficient estimating value $\mu_\gamma$ is rendered moderately, gradually close to the road friction coefficient estimating value $\mu_{LOW}$ outputted from the adaptive control road friction coefficient estimating section 2.

When the signal of IMAGE HALT is inputted from the traveling circumstance recognition section 4 and therefore there is high possibility that the vehicle travels on a road surface with low friction coefficient, the road friction coefficient estimating value $\mu_{LOW}$ from the adaptive control road friction coefficient estimating section 2 is promptly adopted. The adaptive control road friction coefficient estimating section 2 can make an accurate estimation of road friction coefficients even when the vehicle travels on a road surface with low friction coefficient. Further, in case where it is recognized that there is high possibility of low friction coefficient road judging from the traveling circumstance recognition section 4, the road friction coefficient estimating value $\mu_\gamma$ is rendered gradually close to the road friction coefficient estimating value $\mu_{LOW}$ to enhance the accuracy of estimation of road friction coefficients.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments which can be embodied without departing from the principle of the invention set out in the appended claims.

What is claimed is:

1. A road friction coefficient estimating apparatus for a vehicle for estimating a friction coefficient of a road surface on which said vehicle travels comprising:

motion parameter detecting means for detecting motion parameters of said vehicle;

low friction coefficient road traveling condition detecting means for detecting a traveling condition indicative of a traveling on said road surface having a low friction coefficient;

low side road friction coefficient estimating means for estimating a low side road friction coefficient according to an adaptive control theory and to a vehicle motion model based on said motion parameters and said traveling condition indicative of a traveling on said road surface having said low friction coefficient; and road friction coefficient estimating means for estimating said road friction coefficient by comparing an actual yaw rate calculated based on said motion parameters, with a high friction coefficient road reference yaw rate calculated according to said motion parameters and a high road friction coefficient established beforehand, and a low friction coefficient road reference yaw rate calculated according to said motion parameters and said low road friction coefficient established beforehand.

2. The road friction coefficient estimating apparatus according to claim 1, further comprising:

traveling circumstance recognition means for detecting traveling circumstances and for outputting a recognition signal indicative of said road surface covered with snow, wherein when said vehicle travels at high speeds said road friction coefficient estimated by said road friction coefficient estimating means itself is rendered close to a road friction coefficient established beforehand on an asphalted road surface, wherein said road friction coefficient estimating means renders said road friction coefficient first estimated by said road friction coefficient estimating means itself close to said low side road friction coefficient when said recognition signal is inputted, and wherein said road friction coefficient estimating means renders said road friction coefficient estimated by said road friction coefficient estimating means itself close to said low side road friction coefficient when said vehicle travels at high speeds and when said recognition signal is inputted.

3. The road friction coefficient estimating apparatus according to claim 1, wherein said road friction coefficient estimating means comprises a high friction coefficient road reference value estimating section for calculating said high friction coefficient road reference yaw rate, a low friction coefficient road reference value estimating section for calculating said low friction coefficient road reference yaw rate, an actual value estimating section for calculating said actual yaw rate, and a yaw rate comparison road friction coefficient estimating section for estimating a present road friction coefficient by comparing said actual yaw rate with said high friction coefficient road reference yaw rate and said low friction coefficient road reference yaw rate.

4. The road friction coefficient estimating apparatus according to claim 1, wherein when said vehicle travels at high speeds said road friction coefficient estimated by said road friction coefficient estimating means itself is rendered close to a road friction coefficient established beforehand on an asphalted road surface.

5. The road friction coefficient estimating apparatus according to claim 1, further comprising:

traveling circumstance recognition means for detecting traveling circumstances and for outputting a recognition signal indicative of said road surface covered with snow, wherein said road friction coefficient estimating means renders said road friction coefficient first estimated by said road friction coefficient estimating means itself close to said low side road friction coefficient when said recognition signal is inputted.

6. The road friction coefficient estimating apparatus according to claim 2, wherein said road friction coefficient estimated by said road friction coefficient estimating means itself is rendered close to one of said road friction coefficient established beforehand and said low side road friction coefficient.

7. The road friction coefficient estimating apparatus according to claim 4, wherein said road friction coefficient estimated by said road friction coefficient estimating means itself is rendered gradually close to said road friction coefficient established beforehand.

8. The road friction coefficient estimating apparatus according to claim 5, wherein said road friction coefficient estimated by said road friction coefficient estimating means itself is rendered gradually close to said low side road friction coefficient.

9. A road friction coefficient estimating apparatus for a vehicle for estimating friction coefficient of a road surface on which said vehicle travels comprising:

motion parameter detecting means for detecting motion parameters of said vehicle;

traveling circumstance recognition means for detecting traveling circumstances and for outputting a recognition signal indicative of said road surface covered with snow;

low friction coefficient road traveling condition detecting means for detecting a traveling condition indicative of a traveling on said road surface having low friction coefficient;

low side road friction coefficient estimating means for estimating a low side road friction coefficient according to an adaptive control theory and to a vehicle motion model based on said motion parameters and said traveling condition indicative of a traveling on said road surface having low friction coefficient; and road friction coefficient estimating means for estimating a road friction coefficient based on said motion parameters, and for rendering said road friction coefficient itself close to said low side road friction coefficient when said recognition signal is inputted.

10. The road friction coefficient estimating apparatus according to claim 9, wherein said road friction coefficient estimated by said road friction coefficient estimating means itself is rendered gradually close to said low side road friction coefficient.

11. A road friction coefficient estimating apparatus for a vehicle for estimating road friction coefficient of a road surface an which said vehicle travels comprising:

a motion parameter detecting unit for detecting motion parameters of said vehicle; and a road friction coefficient estimating unit for estimating said road friction coefficient based on said motion parameters, and for rendering the estimated road friction coefficient itself close to a specific road friction coefficient when said vehicle travels at high speeds, the specific road friction coefficient being established beforehand on an asphalted road surface.

12. The road friction coefficient estimating apparatus according to claim 11, wherein said road friction coefficient estimated by said road friction coefficient estimating means itself is rendered gradually close to said specific road friction coefficient established beforehand.

13. A method of estimating a road friction coefficient for a road surface, said method comprising:

detecting a motion parameter for a vehicle;

detecting a traveling condition indicative of a traveling on said road surface having low friction coefficient;

estimating a low side road friction coefficient according to an adaptive control theory and to a vehicle motion model based on said motion parameter and said traveling condition indicative of a traveling on said road surface having low friction coefficient; and estimating said road friction coefficient by comparing an actual yaw rate calculated based on said motion parameter, with a high friction coefficient road reference yaw rate calculated according to said motion parameter and a high road friction coefficient established beforehand and with a low friction coefficient road reference yaw rate calculated according to said motion parameter and a low road friction coefficient.

14. The method according to claim 13, further comprising:

detecting traveling circumstances and generating a recognition signal indicative of said road surface covered with snow, wherein said road friction coefficient is rendered close to said low side road friction coefficient when said recognition signal is inputted.

15. The method according to claim 13, wherein when said vehicle travels at high speeds said road friction coefficient is rendered close to a road friction coefficient established beforehand on an asphalted road surface.

16. The method according to claim 14, wherein said road friction coefficient is rendered close to said low side road friction coefficient when said vehicle travels at high speeds and when said recognition signal is inputted.

17. A friction coefficient estimating apparatus for estimating a friction coefficient of a road surface, said apparatus comprising:

a motion parameter detector for detecting a motion parameters for a vehicle traveling on said road surface;

a low friction coefficient traveling condition detector for detecting a traveling condition indicative of a traveling on said road surface having a low friction coefficient;

a low side friction coefficient estimator for estimating a low side friction coefficient according to an adaptive control theory and to a vehicle motion model based on said motion parameter and said traveling condition indicative of a traveling on said road surface having a low friction coefficient; and a friction coefficient estimator for estimating said friction coefficient by comparing an actual yaw rate calculated based on said motion parameters, with a high friction coefficient reference yaw rate calculated according to said motion parameters and a high friction coefficient established beforehand, and a low friction coefficient reference yaw rate calculated according to said motion parameters and a low friction coefficient established beforehand.

* * * * *